United States Patent
Kreuter et al.

[11] Patent Number: 6,117,454
[45] Date of Patent: *Sep. 12, 2000

[54] DRUG TARGETING TO THE NERVOUS SYSTEM BY NANOPARTICLES

[75] Inventors: Jorg Kreuter, Bad Homburg, Germany; Renad N. Alyautdin; Dimitri A. Karkevich, both of Moscow, Russian Federation; Bernhard A. Sabel, Berlin, Germany

[73] Assignee: Medinova Medical Consulting GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/863,122

[22] Filed: May 27, 1997

Related U.S. Application Data

[63] Continuation of application No. 08/556,125, Nov. 9, 1995, abandoned, which is a continuation of application No. 08/203,326, Feb. 28, 1994, abandoned.

[51] Int. Cl.⁷ .............................. A61K 9/52; A61K 9/51
[52] U.S. Cl. ..................... 424/490; 424/489; 424/491; 424/492; 424/493; 424/496; 424/497; 424/498
[58] Field of Search ....................... 424/489–498

[56] References Cited

U.S. PATENT DOCUMENTS

| | | | |
|---|---|---|---|
| 3,957,662 | 5/1976 | Sangekar | 252/11 |
| 4,107,288 | 8/1978 | Oppenheim et al. | 424/22 |
| 4,801,575 | 1/1989 | Pardridge | 514/4 |

(List continued on next page.)

FOREIGN PATENT DOCUMENTS

| | | |
|---|---|---|
| 0 486 959 | 5/1992 | European Pat. Off. . |
| 0056423 | 4/1982 | Japan . |
| WO 89/01343 | 2/1989 | WIPO . |
| WO 89/07938 | 9/1989 | WIPO . |
| WO 91/04014 | 4/1991 | WIPO . |
| WO 91/16064 | 10/1991 | WIPO . |
| WO 92/18529 | 10/1992 | WIPO . |
| 94/02122 | 2/1994 | WIPO . |

OTHER PUBLICATIONS

Banks, W.A. et al., "Delivering Peptides to the Central Nervous System: Dilemmas and Strategies" *Pharm. Res.*, vol. 8, pp. 1345–1350, 1991.

Banks, W.A. and A.J. Kastin, "Peptide Transport System for Opiates Across the Blood–Brain Barrier" (Editorial Review) *Am. J. Physiol.*, vol. 259, E1–E10, 1990.

Banks, W.A. and A.J. Kastin, "Peptides and the Blood–Brain Barrier: Lipophilicity as a Predictor of Permeability" *Brain Res. Bull.*, vol. 15, pp. 287–292, 1985.

Gilman et al., "Goodman and Gilman's—The Pharmacological Basis of Therapeutics" New York: Pergamon Press, 1990 (full text, no copy).

Houghton, R.A. et al., "β–Endorphin: Stability, clearance behavior, and entry into the central nervous system after intravenous injection of the tritiated peptide in rats and rabbits" *Proc. Natl. Acad. Sci. USA*, vol. 77, pp. 4588–4591, Aug. 1980.

Kalenikova et al., Farmakokinetika dalargina, *Vopr. Med. Khim.*, vol. 34, pp. 75–83, 1988.

(List continued on next page.)

*Primary Examiner*—Gollamudi S. Kishore
*Attorney, Agent, or Firm*—Lahive & Cockfield, LLP

[57] ABSTRACT

A novel method of delivering drugs and diagnostics across the blood-brain barrier or blood-nerve barrier is disclosed. Drugs or diagnostic agents are incorporated into nanoparticles which have been fabricated in conventional ways. These nanoparticles are then coated with additional surfactant and given to the body of animals or humans. This allows drugs or diagnostic agents to cross the blood-brain barrier (bbb) to achieve one or more of the following benefits: (1) reducing the dose of a therapeutic drug or diagnostic agent which, when given peripherally, maintains the biological or diagnostic potency in the nervous system, (2) allowing drugs that normally do not cross the bbb to penetrate into the nervous system, and (3) reducing the peripheral side effects by increasing the relative amount of the drug reaching the brain.

13 Claims, 3 Drawing Sheets

U.S. PATENT DOCUMENTS

| | | | |
|---|---|---|---|
| 4,866,042 | 9/1989 | Neuwelt | 514/44 |
| 4,880,816 | 11/1989 | Bodor | 514/307 |
| 4,883,666 | 11/1989 | Sabel et al. | 424/422 |
| 4,902,505 | 2/1990 | Pardridge et al. | 424/85.7 |
| 4,904,479 | 2/1990 | Illum | 424/490 |
| 4,925,673 | 5/1990 | Steiner et al. | 424/455 |
| 4,933,324 | 6/1990 | Shashoua | 514/17 |
| 5,004,697 | 4/1991 | Pardridge | 436/547 |
| 5,017,566 | 5/1991 | Bodor | 514/58 |
| 5,019,400 | 5/1991 | Gombotz et al. | 424/497 |
| 5,059,415 | 10/1991 | Neuwelt | 424/9 |
| 5,112,596 | 5/1992 | Malfoy-Camine | 424/2 |
| 5,124,146 | 6/1992 | Neuwelt | 424/85.8 |
| 5,133,908 | 7/1992 | Stainmesse et al. | 264/4.1 |
| 5,154,924 | 10/1992 | Friden | 424/85.91 |
| 5,182,107 | 1/1993 | Friden | 424/85.91 |
| 5,187,158 | 2/1993 | Bodor | 514/13 |
| 5,213,812 | 5/1993 | Ruiz | 424/499 |
| 5,260,210 | 11/1993 | Rubin et al. | 435/240.23 |
| 5,260,308 | 11/1993 | Poduslo et al. | 514/21 |
| 5,271,945 | 12/1993 | Yoshioka et al. | 424/489 |
| 5,320,906 | 6/1994 | Eley | 424/402.2 |

OTHER PUBLICATIONS

Kreuter, J., "Nanoparticles–preparation and Applications" in M. Donbrow (Ed.) *Microcapsules and Nanoparticles in Medicine and Pharmacy* Boca Raton, FL: CRC Press, pp. 125–148, 1991 (no copy).

Kreuter, J. and H.R. Hartmann, "Comparative Study on the Cytostatic Effects and the Tissue Distribution of 5–fluorouracil in a free–form and bound to polybutylcyanoacrylate nanoparticles in sarcoma 180–bearing mice" *Oncology*, vol. 40, pp. 363–366, 1983.

Levin, E.R. et al., "Studies on Penetration of the Blood–Brain Barrier by Atrial Natriuretic Factor" *Biochem. Biophys. Res. Comm.*, vol. 147, pp. 1226–1231, Sep. 30, 1987.

Marty, J.J. and R.C. Oppenheim, "Collodial Systems for Drug Delivery" *Australian J. Pharm. Sci.*, vol. 6, pp. 65–76, 1977(no copy).

Raeissi, S. and K.L. Audus, "In Vitro Characterization of Blood–brain Barrier Permeability to Delta Sleep–inducing Peptide" *J. Pham. Phy.*, vol. 41, pp. 848–852, 1989.

Saija, A., "Arecoline, but not haloperidol, produces changes in the permeability of the blood–brain barrier in the rat" *J. Pharm. Pharmacol.*, vol. 42, pp. 135–138, 1990.

Sakane, T. et al., "The effect of polysorbate 80 on brain uptake and analgesic effect of D–kyotorphin" *Int. J. Pharm.*, vol. 57, pp. 77–83, 1989.

Sucker, H. et al., Pharmazeutische Technologie, George Thieme Verlag, 1978 (no copy).

Tröster, S.D. et al., "Modification of the body distribution of poly (methyl methacrylate) nanoparticles in rats by coating with surfactants" *Int. J. Pharm.*, vol. 61, pp. 85–100, 1990.

Widder, K.J. et al., "Magnetic Microspheres: Synthesis of a Novel Parenteral Drug Carrier" *J. Pharm. Sci.*, vol. 68, pp. 79–82, Jan. 1979.

Zlokovich, B.V., "In Vivo Approaches for Studying Peptide Interaction at the Blood Brain Barrier" *J. Control Rel.*, vol. 13, pp. 185–201, 1990 (no copy).

Zlokovich, B.V. et al., "Saturable Mechanism for Delta Sleep–Inducing Peptide (DSIP) at the Blood–Brain Barrier of the Vasculary Perfused Guinea Pig Brain" *Peptides*, vol. 10, pp. 249–254, 1989.

DRUG TARGETING TO THE NERVOUS SYSTEM BY NANOPARTICLES

This application is a continuation of Ser. No. 08/556,125 filed on Nov. 9, 1995 now abandoned, which is a continuation of Ser. No. 08/203,326 filed Feb. 28, 1994 now abandoned.

FIELD OF THE INVENTION

This invention relates to both a novel and useful method of targeting and delivering drugs and diagnostics to the brain and a drug targeting system itself. More particularly, the invention pertains to a nanosphere drug targeting system which allows any drug ("drug as used herein includes any substance given for therapeutic and/or diagnostic purposes) to cross the blood-brain barrier (bbb) to achieve one or more of the following benefits: reducing the dose of a drug or diagnostic given peripherally, allowing drugs that normally do not cross the bbb to penetrate into the brain, and reducing the peripheral side effects by improving the relative amount of the drug reaching the brain.

BACKGROUND OF THE INVENTION
General Pharmacology Principles of BBB

The treatment of nervous system disorders can be achieved by giving drugs which affect nervous system function or dysfunction in animals or patients. Typically, such drugs are given by peripheral application, either via the oral or the systemic route. While many drugs are able to cross the bbb, others do not pass the bbb efficiently or not at all and are only effective when given directly into the brain. The term "blood-brain barrier" or "bbb", as used herein, refers to the bbb proper as well as to the blood-spinal barrier. The blood-brain barrier, which consists of the endothelium of the brain vessels, the basal membrane and neuroglial cells, acts to limit penetration of substances into the brain. Sometimes the structure of the bbb is subdivided into two components: the endothelial or capillary barrier and the ependymal barrier Banks, W. A., Kastin, A. J., Barrera, "Delivering peptides to the central nervous system: Dilemmas and strategies," *Pharm. Res.* 8:1345–1350(1991). The nature of the substance penetration through the bbb has not yet been determined but it is known that many of the regulators of brain function such as cytokines, transferrin, encephalins and endorphines can pass through the bbb from the blood vessels into the brain Raeissi, S., Audus, J., "In vitro characterization of blood-brain barrier permeability to delta sleep-inducing peptide." *J. Pharm. Phy.* 41:848–852 (1989); Zlokovich, B., Susie, V. T., Davson, H. Begley, D. J., Jankov, R. M., Mitrivic, B. M., Lipovac, M. N., "Saturable mechanism for delta sleep-inducing peptide (DSIP) at the blood-brain barrier of the vascularly perfused guinea pig brain." *Peptides* 10:249–254(1989); and Zlokovich, B., "In vivo approaches for studying peptide interaction at the blood-brain barrier." *J. Control. Rel.* 13:185–201(1990). However, many substances which can affect the Central Nervous System (or CNS) such as adenosine, β-endorphin, synthetic analogs of endogenous peptides Houghten, R. A. Swann, R. W., Li, C. H., "β-Endorphin: Stability, clearance behaviour and entry into the central nervous system after intravenous injection of the tritiated peptide in rats and rabbits." *Proc. Natl. Acad. Sci. USA* 77:4588–4591(1980); Levin, E. R., Frank, H. J. K., Weber, M. A., Ismail, M., Mills M., "Studies on penetration of the blood-brain barrier by atrial natriuretic factor." *Biochem. Biophys. Res. Commun.* 147:1226–1231(1987) Sakane, T., Tanaka, C., Yamamoto, A., Hashida, M., Sesaki, H., Ueda, H., Takagi, H., "The effect of polysorbate 80 on brain uptake and analgesic effect of D-kyoto."*Int. J. Pharm.* 57:77–83(1989), as well as some excitatory and inhibitor amino acids and trophic factors, penetrate poorly or not at all through the bbb. At present, drugs with no bbb penetration or poor bbb penetration can only be given by direct CNS infusion or by implantation of controlled-release polymers. (See, e.g., U.S. Pat. No. 4,883, 666, Sabel et al.) Thus, many potentially potent drugs are not useful clinically due to their inability to pass the bbb.

In addition, many drugs exist today which affect the brain in a desirable manner but cannot be used because they have severe side effects because they affect peripheral organs of the body and/or the peripheral nervous system. Because of this there is a long-felt need to reduce the side effects of drugs directed to the CNS while reducing the drugs' activity in peripheral organs and increasing the action in the nervous system.

Overcoming the BBB by Difference Approaches

One way to overcome these limitations of traditional drug therapy is to increase the relative amount of drug which passes the bbb. The reasoning is that if one can increase the amount of the drug crossing the bbb while reducing the peripheral dose of a given drug or diagnostic substance, the peripheral side effects of the drug are also less severe, while at the same time maintaining the desired effect in the brain.

A number of approaches have been described in the prior art to increase drug penetration through the bbb.

One approach has been to alter the function of the bbb itself. For instance, osmotic agents, when given peripherally (such as by intravenous injection), result in the opening of the bbb. Further, some drugs acting on the CNS can change the permeability of the bbb for other substances; cholinomimetic arecolines, for instance, have been reported to induce changes of drug penetration through the bbb Saija, A., Princi, P., De Pasquale, R., Costa, G., "Arecoline but not haloperidol produces changes in the permeability of the blood-brain barrier in the rat." *J. Pharm. Pha.* 42:135–138 (1990).

Other drugs which can be given to alter the permeability of the bbb are disclosed in U.S. Pat. Nos. 5,059,415 and 5,124,146, both issued to E. A. Neuwelt. Bradykinin is one specific drug with such effects. (U.S. Pat. No. 5,112,596, issued to Malfroy-Camine). Another method comprises giving permeabilizer peptides such as A-7 or conformational analogs thereof. (WO 92/18529, an application of J. W. Kozarich et al.). A relatively invasive method has been proposed by A. Tomasz and E. Tuomanen (WO 91/16064) who give parenteral injections of purified cell wall or cell wall fragments of eubacteria such as *Streptococcus pneumoniae* to open the bbb.

U.S. Pat. No. 5,260,210 issued to L. L. Rubin et al., discloses a method whereby the permeability of the blood-brain barrier is increased by giving an agent which reduces or interferes with cyclic AMP concentrations or which increases cyclic GMP concentrations.

Any method of changing the permeability of the bbb itself, however, is compromised by the fact that unwanted molecules which the brain is normally protected from by the bbb can pass the bbb as well and exert undesirable side effect. Further, such an effect is non-specific so these methods are impractical due to unpredictable and uncontrollable consequences to the nervous tissue.

Another approach is the modification of the drug molecules themselves. For instance, macromolecules, such as proteins, do not pass the bbb at all. For example, one can first isolate the macromolecule active site, i.e., the portion of the molecule which triggers the biologically desirable event, and then use only this active site. Since size is one of the factors in allowing permeability of the bbb, the reduced size is used in the hope that the smaller molecule can now pass the bbb. Other modifications to macromolecules to attempt passage of the bbb include glycating the proteins, thereby enhancing their permeability of the bbb, or forming a prodrug. U.S. Pat. No. 5,260,308, issued to J. F. Podusio and G. L. Curran, discusses glycating proteins, while U.S. Pat. No. 4,933,324 and WO 89/07938, both on applications of V. E. Shashoua, disclose formation of a prodrug. These prodrugs are formed from a fatty acid carrier and a neuroactive drug which is unable to pass across the bbb on its own. A similar system is disclosed in WO 89/07938.

Still another approach is the implantation of controlled release polymers which release the active ingredient from a matrix-system directly into the nervous tissue. However, this approach is invasive and requires surgical intervention if implanted directly into the brain or spinal cord (see Sabel et al. U.S. Pat. No. 4,883,666; and Sabel et al. U.S. patent application Ser. No. 07/407,930.)

To overcome these limitations, another approach has been tried in which drug carrier systems are used such as liposomes, erythrocyte ghosts, antibody-conjugates, and monoclonal antibody conjugates. One of the major problems in targeted drug delivery is the rapid opsonization and uptake of injected carriers by the reticuloendothelial system (RES), especially by the macrophages in the liver and spleen. This obstacle may be partially overcome in the case of liposomes by incorporation of so-called "stealth" lipids, such as phosphatidylinositol, monosialoganglioside, or sulfogalactosylceramide. However, all of these systems lack the versatility to permit a wide-range application in medicine. These systems are all rather specific for particular purposes or particular drugs or diagnostic agents as the discussion of the prior art disclosures now documents:

U.S. Pat. Nos. 5,182,107 and 5,154,924, both issued to P. M. Friden, teach a method conjugating a drug with an antibody wherein said antibody is reactive with a transferrin receptor. Transferrin receptors are located on brain capillary endothelial cells, which thus transport a drug, such as nerve growth factor, across the bbb. U.S. Pat. No. 5,004,697 (issued to Pardridge) improves such an antibody-conjugate method by providing cationized antibodies with a specific isoelectric point (see also WO 89/01343 by Pardridge).

Another approach is to create chimeric peptides to which the active agents are conjugated (U.S. Pat. No. 4,801,575, also issued to Pardridge). Such a system is further discussed also in U.S. Pat. No. 4,902,505, issued to Pardridge and Schimmel, in which the chimeric peptide, such as histone, is capable of crossing the bbb by transcytosis.

U.S. Pat. Nos. 5,187,158 and 5,017,566, both issued to N. S. Bodor, disclose a brain-specific drug delivery method wherein a centrally acting drug is given with the reduced, biooxidizable lipoidal form of a dihydropyridine reaction-pyridine salt redox carrier such as dopamine. (See also U.S. Pat. No. 4,880,816, also issued to Bodor).

A rather invasive approach is taken to deliver genetic material to the brain. This is done by chemically disrupting the bbb and then using viruses to deliver genes across the bbb. (See, U.S. Pat. No. 4,866,042, issued to E. A. Neuwelt). Here, a corrective genetic material is incorporated into a virus and the virus is then injected into the bloodstream.

Finally, yet another carrier system to deliver drugs across the bbb is the use of liposomes, as disclosed by F. D. Collins and R. C. Thompson (WO 91/04014). Here, liposomes are targeted to specific endogenous brain transport systems which transport specific ligands across the bbb. However, this system does not allow "non-penetrating" drugs to pass the bbb at all and is therefore very different from the present invention.

In summary, while only the carrier system described above leaves the molecule of the bbb themselves intact, the prior art approaches are rather limited in that they apply only to specific drugs in specific circumstances. With regard to the liposomes, which is probably the least invasive method to date to carry drugs across the bbb, there are a number of problems associated with them which have not been overcome by the prior art. Many of these prior art approaches display an unacceptable instability. For example, liposomes often exhibit severe stability problems and are therefore only of limited clinical use.

Thus, only liposomes so far are able to achieve improved bbb penetration of drugs. However, because of the well known disadvantages of instability and their incompatibility with many drugs such as amphiphilic drugs and other agents, including many proteins and glycoproteins, their clinical use is severely compromised.

Rationale for this Patent

Based on these considerations, a critical and long-felt need is apparent from the foregoing presentation for a method that allows drugs which do not pass the bbb (hereafter referred to as "non-penetrating drugs") to become penetrable with features which overcome the disadvantages of the prior art devices, particularly the liposomes. In a similar scope, it is also desirable to improve the rate of penetration of drugs that normally do pass the bbb (hereafter referred to as "penetrating drugs") in order to reduce the peripheral side effects, while at the same time maintaining the desired effect(s) in the nervous system.

The subject of the present invention is a method, composition and drug targeting system using surfactant coated nanoparticles as a drug carrier (or targeting molecule) for a wide range of drugs in order to enhance the penetration of drugs or diagnostic agents across the bbb.

Accordingly, it is an object of this invention to provide a method and composition for the administration of drugs affecting the nervous system to produce a physiologic or pharmacologic effect, or to apply substances with diagnostic value, which overcomes the aforesaid disadvantages associated with the prior art methods and devices.

Still another object of the present invention is to provide a method and composition for allowing non-penetrating and penetrating drugs to pass the bbb more easily.

Yet another object of the invention is to provide for a reliable and easily used method and composition for treating disorders of the nervous system by systemic injection or oral application of drug-absorbed nanoparticles.

A further object of the invention is to provide a method to increase drug transport when injected directly into the nervous system.

Finally, another object of the present invention is to provide a process for preparing the nanoparticles of the present invention.

These and other objects and features of the invention will be apparent from the detailed description and the drawings.

SUMMARY OF THE INVENTION

The present invention features a method of delivering pharmacologically active substances across the blood-brain barrier and a drug targeting system useful for delivering drugs across the bbb. This invention is based on the surprising finding that treatment of nanoparticles having a drug absorbed, adsorbed, or incorporated therein with a sufficient coating of an appropriate surfactant allows the adsorbed drug to traverse the bbb. While it is theorized that the nanoparticles cross the bbb and that the drug desorbs after transit of the nanoparticles, this step is not a necessary part of the invention so long as the drug traverses the bbb to yield its pharmacological action. The term "pharmacologically active," as used herein, means and includes not just drug pharmaceutical activity but also diagnostic activity.

The basic drug targeting system is made by the following process. This process comprises:
 a. Formation of a suspension of nanoparticles by polymerization or dispersion
 b. Sorption of an active ingredient to the nanoparticle, and
 c. coating such nanoparticles with one or more layers of an appropriate surfactant.

More particularly, the method of the invention has the steps of loading a pharmacologically active substance such as a drug onto a nanoparticle, coating the loaded nanoparticle with a surfactant capable of directing the drug across the bbb, administering the coated nanoparticle to a mammal in a manner which allows the drug to reach and cross the bbb, and allowing the drug to be released from the nanoparticle to achieve the desired pharmacological effect. It is not clear if the nanoparticle itself crosses the bbb or whether only the drug crosses by being released from the nanoparticle. However, the exact method is unimportant so long as the pharmacological effect is achieved.

The nanoparticle, which is a synthetic polymeric particle from about 1–1000 nm in diameter, is loaded with the drug by any known loading means. Commonly, solid nanoparticles are used and are loaded by sorption of the drug onto the surface of the nanoparticle, e.g., by soaking the preformed nanoparticle in a solution of the drug. However, in some circumstances, the drug is added to the polymerization solution and the drug is incorporated into the nanoparticle as the nanoparticle is made. The critical, innovative step is that after drug absorption or incorporation, the nanoparticles are coated with surfactants by incubating them in surfactant-solution under appropriate conditions. The surfactant allows penetration of the bbb by the drug without physical modification of the nanoparticle or the drug itself. A preferred surfactant is Polysorbate 80.

The critical and novel step of the process and composition of this invention is to monitor the time that is allowed for the surfactant to associate with a surface of the nanoparticles. Simply mixing is not sufficient to enable passage of the bbb by the drug. A major advantage of the system and method is that it can be used to transport drugs which could not otherwise cross the bbb into the central nervous system.

The drug targeting system of the invention provides the means of carrying out the method. This drug targeting system includes the drug-loaded nanoparticles which are coated with the appropriate surfactant, possibly carried in a suitable buffer or other physiologically acceptable carrier solution. The type of carrier, and its properties, depend on how the nanoparticles are to be administered, e.g., orally, intravenously, intramuscularly or in so other manner. A very broad range of drugs can be delivered in this system and determining the optimum mode of targeting depends on the system selected.

Other objects, features and advantages of the invention will be apparent to those versed in the art from the detailed description of the specification which will now follow, taken in conjunction with the tables, drawings, and the accompanying claims.

BRIEF DESCRIPTION OF THE DRAWINGS

The drawings are not drawn to scale. They are set forth to illustrate various embodiments of the inventions and the results achieved, the drawings, to which reference will be made, are as follows:

FIG. 1 is a schematic drawing of the nanoparticle, indicating its molecular structure.

DETAILED DESCRIPTION OF THE INVENTION

It should be understood that the detailed description and specific examples, while indicating preferred embodiments of the invention, are given by way of illustration only, since various changes and modifications within the spirit and scope of the invention will become apparent to those skilled in the art from this description and the accompanying claims.

What are Nanoparticles?

The term "nanoparticle" as used herein denotes a carrier structure which is biocompatible with and sufficiently resistant to chemical and/or physical destruction by the environment of use such that a sufficient amount of the nanoparticles remain substantially intact after injection into the blood stream, or given intraperitoneally or orally, so as to be able to reach the brain at the bbb. If the drug can cross the bbb in the form whereby it is adsorbed to the nanoparticles, they must also remain sufficiently intact to cross the bbb. Usually, nanoparticles are solid colloidal particles ranging in size from 1 to 1000 nm. Drugs or other relevant materials (e.g., those used for diagnostic purposes in nuclear medicine or in radiation therapy) can be dissolved within the nanoparticles, entrapped, encapsulated and/or adsorbed or attached.

General Matters Relating to the Fabrication of Nanoparticles

Nanoparticles can be made from a broad number of materials including acrylates, methacrylates, methylmethacrylates, cyanoacrylates, acrylamides, polyacetates, polyglycolates, polyanhydrides, polyorthoesters, gelatin, polysaccharides, albumin, polystyrenes, polyvinyls, polyacroleines, polyglutataldehydes, and derivatives, copolymers, and derivatives thereof. Monomer materials particularly suitable to fabricate biodegradable nanoparticles by emulsion polymerization in a continuous aqueous phase include methylmethacrylates, polyalkycyanoacrylates, hydroxyethylmethacrylates, methacrylate acid, ethylene glycol dimethacrylate, acrylamide, N, N'-bismethyleneacrylamide and 2-dimethylaminoethyl methacrylate. Other nanoparticles are made by different techniques from N, N-L-lysinediylterephthalate, alkylcyanoacrylate, polylactic acid, polylactic acid-polyglycolic acid-copolymer, polyanhydrates, polyorthoesters, gelatin, albumin, and desolvated macromolecules or carbohydrates. Further, non-biodegradable materials can be used such as polystyrene, poly (vinylpyridine), polyacroleine and polyglutaraldehyde. A summary of materials and fabrication methods for making nanoparticles has previously been published. See Kreuter, J. (1991) "Nanoparticles-preparation and applications." In: M. Donbrow (Ed.) "Microcapsules and nanoparticles in medicine and pharmacy." CRC Press, Boca Raton, Fla., pp. 125–148.

General Process of Fabrication

Nanoparticles can be produced by conventional methods, including emulsion polymerization in a continuous aqueous phase, emulsion polymerization in continuous organic phase, interfacial polymerization, solvent deposition, solvent evaporation, dissolution of an organic polymer solution, cross-linking of water-soluble polymers in emulsion, dissolution of macromolecules, and carbohydrate cross-linking. These fabrication methods can be performed with a wide range of polymer materials mentioned above.

The present invention teaches a process for preparation of coated nanoparticles which comprises:

a. Formation of a suspension of nanoparticles, e.g., by polymerization or dispersion b. Sorption or incorporation of an active ingredient to the nanoparticle, and c. coating such nanoparticles with one or more layers of an appropriate surfactant.

The drug or a diagnostic agent can either be adsorbed (or absorbed) to a premade nanoparticle or it can be incorporated into the nanoparticle during the manufacturing process. Methods of absorption, adsorption, and incorporation are common knowledge to those skilled in the art.

Typical materials suitable for coating of the nanoparticles are surfactants selected from a group comprising fatty acid esters of glycerols, sorbitol and other multifunctional alcohols, as, for instance, glycerol monostearate, sorbitan monolaurate, or sorbitan monoleate; polysorbates, as, for instance, polysorbate 80 and polysorbate 60; poloxamers, as, for instance, poloxamer 188, 338, or 407; poloxamines, such as poloxamine 904 or 1508; polyoxyethylene ethers and polyoxyethylene esters; ethoxylated triglycerides; ethoxylated phenols and ethoxylated diphenols; surfactants of the Genapol TM and Bauki series; metal salts of fatty acids, metal salts of fatty alcohol sulfates, sodium lauryl sulfate; and metal salts of sulfosuccinates. Other surfactants are known which may be useful as coating materials for nanospheres have been described by H. Sucker et al. (Pharmazeutische Technologie, George Thieme Verlag, 1978).

The choice of the monomer and/or polymer, the solvent, the emulsifier and the surfactant and other auxiliary substances will be dictated by the particular nanoparticle being fabricated and can be chosen, without limitation and difficulty, by those skilled in the art. The limiting requirement is that the combination allows passage of the drug across the bbb.

The ratio of the drug to polymer can vary within a wide range. Also, the removal of the solvent or emulsifier can be achieved in a number of different ways.

Nanoparticles as Drug Carriers

The biologically active ingredient (such as a drug) that can be suitably employed in accordance with the invention with warm blooded animals, particularly mammals including human, veterinarian animals, and farm animals, all are those affecting, acting on, or being visualized within the nervous system, including tumor tissue located therein. Also, the use of diagnostic agents is possible. There is essentially no limitation on the type of drug or other ingredient which may be used.

The present invention may be applied to deliver any agent for the treatment of disorders affecting the nervous system and it may also be applied for diagnostic purposes. Preferred classes of agents for treatment of CNS disorders include:

Drugs acting at synaptic and neuroeffector junctional sites; general and local analgesics and anesthetics such as opioid analgesics and antagonists; hypnotics and sedatives; drugs for the treatment of psychiatric disorders such as depression, schizophrenia; anti-epileptics and anticonvulsants; Huntington's disease, aging and Alzheimer's disease; neuroprotective agents (such as excitatory amino acid antagonists and neurotropic factors) and neuroregenerative agents; trophic factors such as brain derived neurotrophic factor, ciliary neurotrophic factor, or nerve growth factor; drugs aimed at the treatment of CNS trauma or stroke; and drugs for the treatment of addiction and drug abuse; autacoids and anti-inflammatory drugs; chemotherapeutic agents for parasitic infections and microbial diseases; immunosuppressive agents and anti-cancer drugs; hormones and hormone antagonists; heavy metals and heavy metal antagonists; antagonists for non-metallic toxic agents; cytostatic agents for the treatment of cancer; diagnostic substances for use in nuclear medicine, and radiation therapy immunoactive and immunoreactive agents; and a number of other agents such as transmitters and their respective receptor-agonists and -antagonists, their respective precursors or metabolites; antibiotics, antispasmodics, antihistamines, antinauseants, relaxants, stimulants, "sense" and "antisense" oligonucleotides, cerebral dilators, psychotropics, anti-manics, vascular dilators and constrictors, anti-hypertensives, migraine treatments, hypnotics, hyper- or hypo-glycemic agents, mineral or nutritional agents, anti-obesity drugs, anabolics and anti-asthmatics.

Typical active ingredients (e.g., drugs) can be any substance affecting the nervous system or used for diagnostic tests of the nervous system. These are described by Gilman et al. (1990), "Goodman and Gilman's—The Pharmacological Basis of Therapeutics", Pergamon Press, New York, and include the following agents:

acetylcholine and synthetic choline esters, naturally occurring cholinomimetic alkaloids and their synthetic congeners, anticholinesterase agents, ganglionic stimulants, atropine, scopolamine and related antimuscarinic drugs, catecholamines and sympathomimetic drugs, such as epinephrine, norepinephrine and dopamine, adrenergic agonists, adrenergic receptor antagonists, transmitters such as GABA, glycine, glutamate, acetylcholine, dopamine, 5-hydroxytryptamine, and histamine, neuroactive peptides;

analgesics and anesthetics such as opioid analgesics and antagonists; preanesthetic and anesthetic medications such as benzodiazepines, barbiturates, antihistamines, phenothiazines and butylphenones; opioids; antiemetics; anticholinergic drugs such as atropine, scopolamine or glycopyrrolate; cocaine; chloral derivatives; ethchlorvynol; glutethimide; methyprylon; meprobamate; paraldehyde; disulfiram; morphine, fentanyl and naloxone;

centrally active antitussive agents;

psychiatric drugs such as phenothiazines, thioxanthenes and other heterocyclic compounds (e.g., halperiodol); tricyclic antidepressants such as desimipramine and imipramine; atypical antidepressants (e.g., fluoxetine and trazodone), monoamine oxidase inhibitors such as isocarboxazid; lithium salts; anxiolytics such as chlordiazepoxyd and diazepam;

anti-epileptics including hydantoins, anticonvulsant barbiturates, iminostilbines (such as carbamazepine), succinimides, valproic acid, oxazolidinediones and benzodiazepines.

anti-Parkinson drugs such as L-DOPA/CARBIDOPA, apomorphine, amantadine, ergolines, selegeline, ropinorole, bromocriptine mesylate and anticholinergic agents;

antispasticity agents such as baclofen, diazepam and dantrolene;

neuroprotective agents, such as excitatory amino acid antagonists, neurotrophic factors and brain derived neurotrophic factor, ciliary neurotrophic factor, or nerve growth factor; neurotrophin(NT) 3 (NT3); NT4 and NT5; gangliosides; neuroregenerative agents;

drugs for the treatment of addiction and drug abuse include opioid antagonists and anti-depressants;

autocoids and anti-inflammatory drugs such as histamine, bradykinin, kallidin and their respective agonists and antagonists;

chemotherapeutic agents for parasitic infections and microbial diseases;

anti-cancer drugs including alkylating agents (e.g., nitrosoureas) and antimetabolites; nitrogen mustards, ethylenamines and methylmelamines; alkylsulfonates; folic acid analogs; pyrimidine analogs, purine analogs, vinca alkaloids; and antibiotics.

The present invention is also useful for the delivery of anti-nauseants, relaxants, stimulants, "sense" and "anti-sense" oligonucleotides, cerebral dilators, psychotropics, vascular dilators and constrictors, anti-hypertensives, migraine treatments, hyper- or hypo-glycemic agents, mineral or nutritional agents, anti-obesity drugs, anabolics and anti-asthmatics, anti-inflammatory drugs such as phenylbutazone, indomethacin, naproxen, ibuprofen, flurbiprofen, diclofenac, dexamethasone, prednisone and prednisolone; cerebral vasodilators such as soloctidilum, vincamine, naftidrofuryl oxalate, co-dergocrine mesylate, cyclandelate, papaverine, nicotinic acid, anti-infective agents such as erythromycin stearate, and cephalexin.

Mechanism of BBB Transport for Nanoparticles

In accordance with the present invention, nanoparticles are able to carry (or deliver) drugs or diagnostics across the bbb. While not being bound by any particular theory, what comprises the mechanism of transport across the bbb and why it is noteworthy and unexpected is that it can not presently be explained by traditional concepts. At the present time, it is not possible to show the concrete mechanism of this peptide penetration across the bbb, although speculations can be made.

Banks et al. (1991) suggested some mechanisms of this peptide transport to the brain which may also apply to nanoparticles or materials carried by nanoparticles. Transport can be achieved by nonsaturable and saturable means, as intact molecules or their metabolites. The degree of bbb passage depends primarily on lipid solubility of the molecule Banks, W. A., Kastin, A. J., "Peptides and blood-brain barrier: Lipophilicity as a predictor of permeability." *Brain Res. Bull.*, 15:287–292(1985). Other factors that may influence brain entry are molecular weight, charge, degree of protein binding in the serum, although these seem to play a lesser role than lipophilicity (Banks et al., 1991). The transport mechanism suggested by Banks seems to be restricted to transporting a limited number of structurally related peptides such as met-encephalin and a few other closely related peptides. They do not apply, for instance, to β-endorphins and cyotorphines. Saturable transport rates are modulated by various factors, including some substances, like leucine and aluminum Banks, W. A., Kastin, A. J., "Editorial review: Peptide transport system for opiates across the blood-brain barrier." *Am. J. Physiol.*, 259:E1–E10 (1990). Whether transport mechanisms of nanoparticles are similar to transport of peptides is not known currently. As the present invention is the first to demonstrate nanoparticle transport to the CNS of a biologically active drug, no further information is available at present.

Specific Material and Process for Fabrication as Example

EXAMPLE 1

In the presently preferred embodiment, the nanoparticles are made of polyacyl cyanoacrylates (hereafter also referred to as "poly butylcyano acrylate") of the general formula:

In the preferred embodiment of the present invention, the nanoparticles were prepared using an acidic polymerization medium containing dextran 70000 as stabilizer (dextran 70000 1% in 0.1 N HCl). In the in vitro study, we used butyl cyanoacrylate which was added to obtain a 1% nanoparticle suspension. The mixture was agitated by stirring with a magnetic stirrer at 500 rpm for 4 h to allow nanoparticle formation. The resulting suspension was neutralized with 0.1 N sodium hydroxide solution, filtered through a sintered glass filter (pore size 10 μm), and 1% of anhydrous glucose was added to improve redispersability of the nanoparticles after lyophilization. Particle size determination was done by means of photon correlation spectroscopy with a BO 20 Goniometer (Brookhaven Instr. Corporation, Holtsville, N.Y.). An average diameter of 230 nm was observed. The nanoparticle suspension was then lyophilized using a Lyovac GT 2 freeze dryer (Leybold AG Köln, Germany).

EXAMPLE 2

An alternative example of a method for nanoparticle fabrication with drug incorporation is the following: In this example, the nanoparticles are prepared using an acidic polymerization medium containing dextran 70000 as stabilizer (dextran 70000 1% in 0.2 N HCl) and 5 mg dalargin. In this in vitro study, we used butyl cyanoacrylate which was added to obtain a 1% nanoparticle suspension. The mixture was agitated by stirring with a magnetic stirrer at 500 rpm for 4 h to allow nanoparticle formation. The resulting suspension was neutralized with 0.1 N sodium hydroxide solution, filtered through a sintered glass filter (pore size 10 μm), and 1% of anhydrous glucose was added to improve redispersability of the nanoparticles after lyophilization.

EXAMPLE 3

This example is yet another method for nanoparticle fabrication with drug sorption. Polylactic polyglycolic acid (PLGA) is dissolved in acetone (10 ml, 20.0 mg/ml) and a mixture of deionized water and ethanol (1: 1) is added dropwise (25 G syringe needle) into the copolymer solution stirred by magnetic stirrer (Ika-Labortechnik, Germany), until turbidity indicative of copolymer precipitation is visually observed. The suspension of these preformed nanospheres is then added to an aqueous surfactant solution (15 ml, 1% w/v) placed in a glass beaker (50 ml) and agitated by a magnetic stirrer at ambient temperature until complete evaporation of the organic solvent has taken place.

EXAMPLE 4

This example shows a method for albumin nanoparticle fabrication with drug sorption. Nanoparticles are prepared using a water in oil emulsification process as described in Widder, K. J., Flouret, G., and Senyei, A. E., "Magnetic microspheres: Synthesis of a novel parenteral drug carrier." *J. Pharm. Sci.* 68:79–82(1979). One half ml of a 25% aqueous bovine serum albumin solution is mixed well with 30 ml ice-cooled (4° C.) cottonseed oil using a magnetic stirrer. The above emulsion is further subjected to ultrasonication (125 W, 1 h, Bransonic 220, Branson, Geneva, CH) while the system is kept ice-cooled. One hundred ml of cottonseed oil is then heated to 145° C.±10° C. (heating mantle 200 W/220 V, Heraeus-Wittmann, Heidelberg, GER) in a 500 ml three-necked round bottom flask (Schott, Mainz, Germany) while stirring is maintained at 1500 rpm (stirring motor type IKA, RW 18, Staufen i. Br., Germany; stirring head MRK1 NS 29/32 Buddeberg, Mannheim, Germany).

The preformed aqueous albumin in oil emulsion is added dropwise (100±10 drops/min.) into the preheated, rapidly stirred cottonseed oil through a needle tip (24 G×¾ Terumo, Frankfurt, Germany) connected to a syringe (20 ml Luer, Braun Melsungen, Germany). Then the preformed albumin spheres are cross-linked by the maintenance of the heat. After ten minutes, the system is allowed to cool to room temperature, while stirring is maintained. The cooled mixture (25° C.) is then diluted with 100 ml of diethylether and centrifuged at 2500 rpm (table centrifuge model GPR, Beckman, München, Germany) for 15 min. The supernatant is discarded and the washing procedure is repeated three times. After evaporation of the solvent, a free flowing powder is obtained which is stored at 4° C. until use.

EXAMPLE 5

Another example of a method for albumin nanoparticle fabrication with drug sorption comprises the following steps: Albumin nanoparticles are produced by desolvation process according to a slightly modified method suggested in Marty, J. J. and Oppenheim, R. C. "Colloidal systems for drug delivery," *Australian J. Pharm. Sci.* 6:65–76(1977). Five hundred mg of albumin (BSA) is dissolved in 40 ml of purified water. About 60 ml of absolute ethanol is added, until the onset of protein desolvation can be visually observed by the rise in turbidity. The system is then cross-linked by addition of 0.1 ml 25% glutaraldehyde and agitated for 1 hr. on a magnetic stirrer (IKA, Heidelberg, Germany). Unreacted glutaraldehyde is destroyed by carefully adding 0.5 ml of an aqueous 12% sodium metabisulfate solution. After a reaction time of another 3–4 hrs., excess ethanol is evaporated under vacuum. The obtained preparation is then further purified by column gel filtration (Sephacryl G 1000, Pharmacia, Sweden). After the addition of 100 mg glucose, the resulting particle suspension is lyophilized for about 16 hours (Lyovac, Heraeus, Hanau, Germany) in order to increase the redispersibilty of the product.

EXAMPLE 6

This example describes a series of experiments to show in vivo activity of the method of the invention. In the presently preferred embodiment of the invention for the in vivo experiment, the drug dalargin was used to determine the usefulness of the current invention and nanoparticles were prepared as described in example 1. The hexapeptide dalargin is a leu-encephalin analog which contains D-Ala in second position in order to prevent enzymatic destruction (Tyr-DAla-Gly-Phe-Leu-Arg).

Generally, dalargin is used as a therapy for peripheral ulcers and from this application it is known that dalargin is stable in the blood stream. The injection of any of the metabolites, on the other hand, has no effect. Independent of its anti-ulcer activity, dalargin exhibits potent analgesic activity following intraventricular injection in the brain. However, it does not produce analgesia when given peripherally (Kalenikova et al., Farmakokinetika dalargina, *Vopr. Med. Khim.* 34:75–83(1988). From this it can be concluded that dalargin, when administered into the blood stream, does not penetrate through the bbb at all or in insufficient amounts to cause CNS action. As the present invention discloses, the appearance of analgesia after the peripheral injection of dalargin-adsorbed nanoparticles shows that nanoparticles are able to carry non-penetrating drugs across the bbb and thus serve as a novel drug transport method to the brain.

The following method is used to achieve "drug loading" of the nanoparticles. The same procedure has also been found to work with the nanoparticles made using the procedures described in examples 3 through 5: One hundred mg of the lyophilized nanoparticles were resuspended in 5 ml phosphate buffered saline (PBS), bisodium phosphate/monobasic potassium phosphate/sodium chloride (7.6/1.45/4.8 w/w/w) containing 0.09% of dalargin. The peptide was allowed to absorb to the nanoparticle surface for three hours. Total amount of the peptide absorbed was calculated by filtering the suspension through a membrane filter of 10 nm pore size (Minisart; Sartorius AG Göttingen, Germany) and measuring the amount of free peptide in the filtrate by means of UV spectrophotometry at 220 nm wavelength. It was shown that 30% of the peptide (1.35 mg) was absorbed to the nanoparticles. The suspension was diluted in PBS to obtain a peptide concentration between 0.25 and 0.75 mg/ml and sonicated for five minutes. After that, the nanoparticles were coated with an appropriate surfactant.

While many coating materials can be used to achieve the desired effect, in the presently preferred embodiment the following coating materials were used: poloxamers 184, 188, 338, 407 (POE-POP-blockcopolymers obtained from C. H. Erbsloeh, Düsseldorf, Germany), poloaxamine 908 (ethylenediamine—POE-POP-blockcopolymer, C. H. Erbesloeh), polysorbates 20 and 80 (Atlas Chemie, Essen, Germany), and Brij 35 (polyethylene 23 lauryl ether, Fluka, Buchs, CH).

To achieve the coating of the drug-absorbed nanoparticles, 1% of surfactant was added to the nanoparticle suspension, incubated for 30 min. and immediately thereafter injected into mice. It is possible to vary the suspension time and the concentration of the surfactant in suspension. All of the surfactants coated the nanoparticles appropriately.

Proof of Concept

To evaluate the biological activity of the drug after absorbing it to nanoparticles and coating them with surfactant, an in vivo assay was used.

In vivo Assay

Figure 1A:
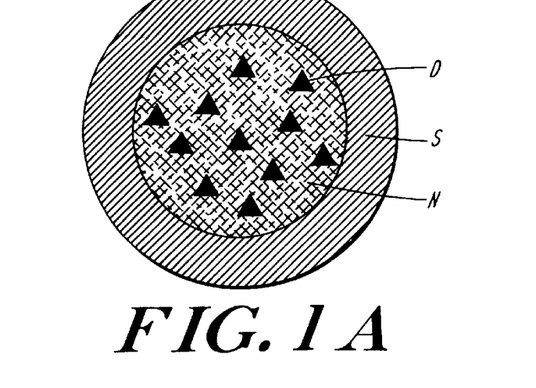
FIG. 1A displays a monolithic nanoparticle (N) with drug dispersed or dissolved in matrix (D) and coated with a surfactant (S).
Figure 1B:
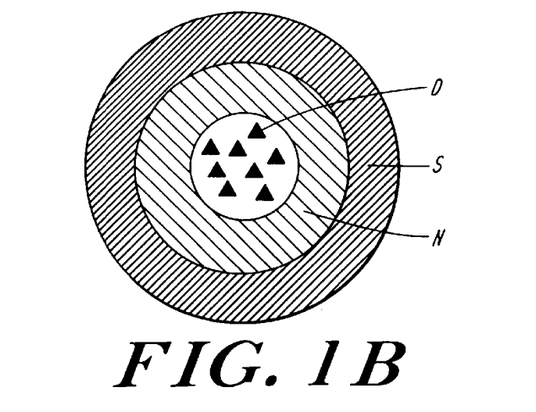
FIG. 1B displays a capsule-type nanoparticle with drug entrapped in the interior with a surfactant coating.
Figure 1C:
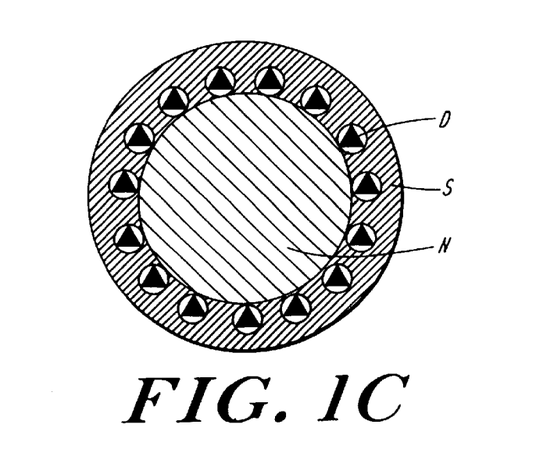
FIG. 1C displays a nanoparticle with surface-absorbed or -adsorbed drug with an additional surfactant coating. These three embodiments are not limiting because combinations thereof are possible. Furthermore, various numbers of coatings can be employed.
Figure 2:
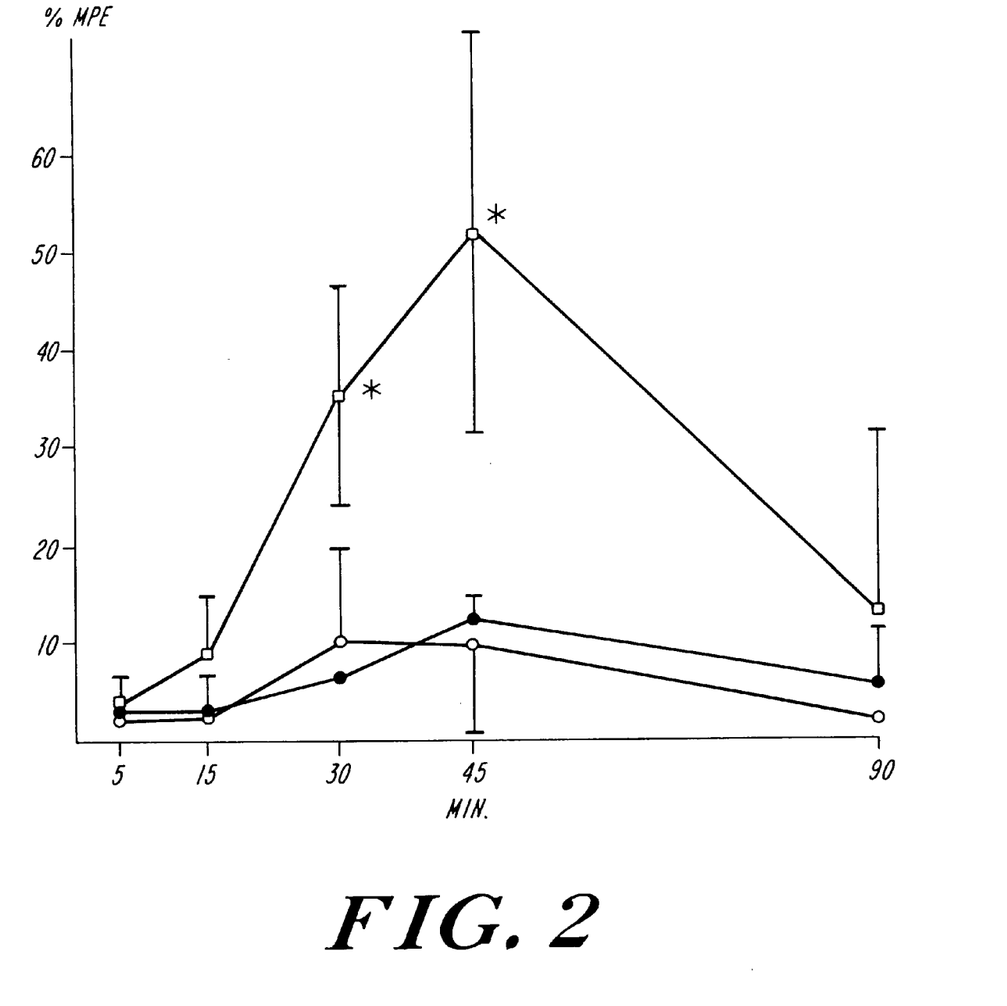
FIG. 2 illustrates the analgesic effect in percent of maximally possible effect (MPE) in tail flick test after intravenous injection of dalargin (10 mg/kg). Dalargin was given either in solution (filled circles), in a simple mixture of drug, nanoparticles, and surfactant (open circle), or after sorptive binding to nanoparticles and coating with polysorbate 80 (at a dose of 7.5 mg dalargin/kg). The data, shown also in Table 1, were collected at different time points following injection.

In order to test the pharmacological usefulness of this approach, we absorbed the nanoparticles with a drug which does not pass the bbb when given systemically, namely, the leu-encephalin analog dalargin. Dalargin is a highly potent analgesic when injected directly into the brain, but it is without any effect when given peripherally. Dalargin was absorbed to poly (butyl cyanoacrylate) nanoparticles and incubated in an aqueous Polysorbate 80 solution for 30 min. After this time, this preparation was injected intravenously into mice at dalargin dosages of 2.5, 5.0, and 7.5 mg/kg. Various preparations include pure dalargin solution, uncoated dalargin nanoparticles, a freshly prepared mixture of nanoparticles, drug, and surfactant without allowing drug or surfactant sorption times as well as pure surfactant or nanoparticle solutions served as controls. Activity threshold was measured with the tail flick test. Dalargin, when dissolved in PBS up to a dose of 10 mg/kg, did not exhibit any analgesic effect after i.v. injection (FIG. 2). In fact, only dalargin absorbed to nanoparticles and coated with Polysorbate 80 had an analgesic activity which became statistically significant at a dose of 5 mg/kg dalargin as indicated by the tail flick test. All other preparations including those containing dalargin up to a dose of 10 mg/kg had no analgesic effect at all. To conduct the proper control experiments, we included the following groups in our studies:

Group 1: suspension of empty nanoparticles (200 mg/kg).

Group 2: Polysorbate 80 solution in PBS.

Group 3: dalargin solution in PBS.

Group 4: mixture of dalargin solution and Polysorbate 80.

Group 5: mixture of dalargin solution and empty nanoparticles.

Group 6: mixture of dalargin, empty particles and Polysorbate 80 after mixing of the drug and surfactant with the particles without any equilibration time.

Group 7: dalargin loaded by incubating for 3 hrs. onto empty nanoparticles and injected without Polysorbate 80 coating.

Groups 8–10: dalargin loaded nanoparticles (2.5, 5.0 and 7.5 mg/kg, respectively) with the Polysorbate 80 coating.

Group 11: dalargin loaded nanoparticles (7.5 mg/kg) with Polysorbate 20 coating.

Group 12: dalargin loaded nanoparticles (7.5 mg/kg) with Poloxamine 908 coating.

The results are displayed in Table 1 and in FIG. 2. None of the control groups (Groups 1–7) exhibited any analgesic effects in the mice which were injected with them. Of particular interest are Groups 11 and 12 which also fail to show analgesic effect. It appears that although these surfactants coat the nanoparticles and can be concentrated in brain tissue, they do not facilitate transport of the drug across the bbb.

TABLE 1

| GROUP | TIME (min) | | | | | | | | | |
|---|---|---|---|---|---|---|---|---|---|---|
| | 5 | | 15 | | 30 | | 45 | | 90 | |
| | mean | SD | mean | SD | mean | SD | mean | SD | mean | SD |
| group 1 | 2.3 | 2.5 | 3.8 | 1.8 | 1.5 | 9.0 | 0.75 | 3.0 | 4 | 4.2 |
| group 2 | 5.0 | 3.9 | 7.0 | 3.3 | 8.0 | 3.6 | 12.0 | 3.1 | 9.0 | 9.1 |
| group 3 | 2.0 | 6.6 | 2.2 | 8.6 | 10.0 | 9.8 | 9.3 | 8.7 | 2.0 | 6.1 |
| group 4 | 4.6 | 1.2 | 4.8 | 1.7 | 8.3 | 2.3 | 7.8 | 2.3 | 6.4 | 2.6 |
| group 5 | 2.5 | 3.0 | 1.3 | 4.6 | 7.5 | 6.2 | 1.5 | 5.4 | 0.25 | 3.3 |
| group 6 | 2.8 | 3.3 | 2.8 | 3.7 | 6.3 | 4.9 | 12.5 | 2.0 | 5.5 | 5.8 |
| group 7 | 1.2 | 1.1 | 2.3 | 1.6 | 4.1 | 1.0 | 3.7 | 1.1 | 4.9 | 1.1 |
| group 8 | 0.25 | 3.5 | 1.7 | 2.8 | 9.3 | 7.0 | 11.6 | 9.7 | 1.6 | 5.3 |
| group 9 | 1.8 | 9.3 | 2.7 | 18.4 | 42 | 30 | 36.8* | 21.5 | 21.0 | 12.4 |
| group 10 | 3.5 | 2.6 | 8.6 | 6.2 | 35.0* | 11 | 51.8* | 20.2 | 12.8 | 18.4 |
| group 11 | — | — | 7.5 | 3.3 | — | — | 7.8 | 3.4 | 6.5 | 2.9 |
| group 12 | — | — | 6.8 | 2.8 | — | — | 6.4 | 3.0 | 3.2 | 3.1 |

*-statistically significant difference

The specificity of the analgesic effect in the brain was documented by application of an opioid antagonist. Nalaxone (0.1 mg/kg) diminished the effectiveness of dalargin bound to Polysorbate 80-coated nanoparticles.

Figure 3:
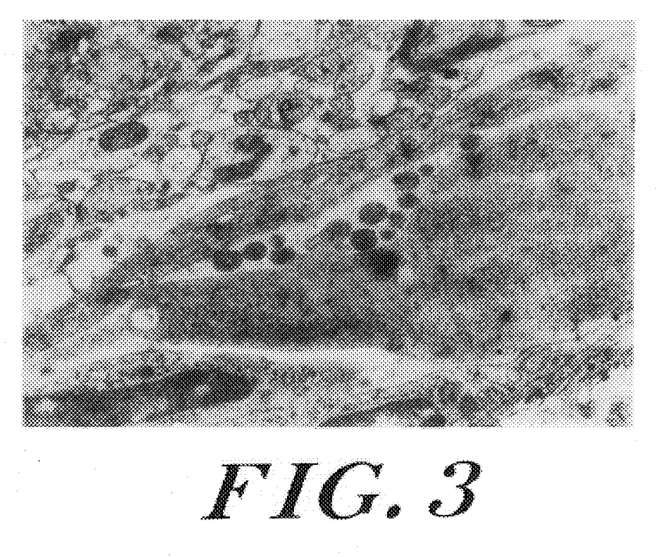
FIG. 3 is an electronmicrograph of nanoparticles in brain tissue. The graph clearly displays the nanoparticles in the capillary lumen.
Figure 4:
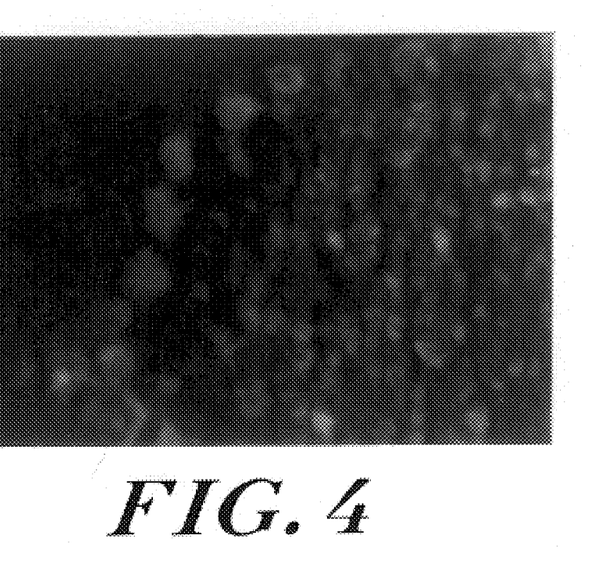
FIG. 4 illustrates Purkinje Cells displaying fluorescence after i.v. injection of fluorescing nanoparticles.

To determine the fate of the nanoparticles, histological investigations were conducted with fluorescein-loaded Polysorbate 80-coated nanoparticles. These studies indicate that the coated nanoparticles were taken up by the endothelial cells lining the brain blood capillaries and seem to be released later into the interior brain compartment. (See FIG. 3 and FIG. 4).

Taken together, these results indicate that a drug, when bound to the appropriately coated nanoparticle, shows a biological effect in the brain (in this specific case leading to analgesia). This is due to a previously impossible passage of the drug through the bbb which could be achieved by one or more of the following mechanisms: enhancement of the transport of the drug through the bbb by diffusion or by an activation of endocytotic uptake by endothelial cells of the brain blood vessels.

Theoretically, there are some possibilities to influence the penetration of drugs through the bbb either by the use of active transport or by passive ways.

Polysorbate 80 is a very interesting substance in this respect for brain targeting and enhancement of the uptake of some substances. Tröster, S. D., Muller, U., Kreuter, J., "Modification of the body distribution of poly (methyl methacrylate) nanoparticles in rats by coating with surfactants." Int. J. Pharm. 61:85–100(1990), demonstrated an increased accumulation of nanoparticle radioactivity in the brain area after i.v. injection of polysorbate 80-coated 14C-poly(methyl methacrylate) nanoparticles. However, the same paper also showed similar uptake with other surfactants in the brain. Since these polymers are only very slowly biodegradable, this accumulation within the time frame of the mentioned study has to be due to intact particles.

However, as mentioned before and as shown in FIG. 2 and Table 1, the simple mixture of nanoparticles with surfactants as used in the Tröster study did not lead to any transport of the drug across the bbb. In an earlier study by Kreuter, J., Hartmann, H. R., "Comparative study on the cytostatic effects and the tissue distribution of 5-fluorouracil in a free form and bound to polybutylcyanoacrylate nanoparticles in sarcoma 180-bearing mice." Oncology 40:363–366(1983), an enhanced 5-fluorouracil accumulation into the brain was observed in comparison to a free solution of the drug after using nanoparticles prepared in a Polysorbate 20-containing medium. At that time, this result did not attract any attention, since the binding to nanoparticles induced an increased 5-fluorouracil concentration in all organs investigated. In addition, the same situation as in the Tröster study likely occurred in that the particles accumulated in the blood stream of the brain without crossing the bbb. As mentioned above, the induction of dalargin activity in the present invention was possible only after binding to nanoparticles and only after attainment of an equilibrium binding of the drug. Mixing of this drug, Polysorbate 80 and the nanoparticles and the i.v. injection immediately after mixing exhibited no drug action at all. This clearly demonstrates that the activity was only due to drug bound to intact particles.

The mechanism of the transport induction could be due to a number of mechanisms. First, nanoparticles may be bound to the inner endothelial lining of the brain capillaries. Subsequently, the nanoparticles would just deliver the drug more efficiently to the brain cells by providing a large concentration gradient and simple diffusion. The second possibility is brain endothelial uptake by phagocytes. As we have shown in the in vitro study above, Polysorbate 80 induces an increased tissue uptake of nanoparticles in brain blood vessel endothelium. Again, the drug could then be delivered by diffusion out of the endothelial cells to the brain cells. Alternatively, but probably less likely, the nanoparticles with the drugs could be exocytosed into the surrounding brain tissue.

The possibility exists that Polysorbate 80, moreover, seems to have bbb-opening properties. Sakane el al. (1989) showed that a 9% solution of Polysorbate 80 provided an enhanced passage of insulin and the dipeptide b-kyotorphin through the bbb in the brain. However, with the in vivo experiment above, we have clearly shown that this can be ruled out as a possible mechanism. Because group 4 (mixture of dalargin solution and Polysorbate 80) did not show analgesia on the tail flick test, the Polysorbate alone does not result in dalargin passage. Thus, our method provides a specific bbb passage method which clearly displays an unexpected improvement over the prior art. The mechanism is not one of nondiscriminant opening of the bbb itself to a CNS-active drug.

What is claimed is:

1. A method of transmitting a pharmacologically active substance across the blood-brain barrier in a mammal to achieve a pharmacological effect in the central nervous system comprising the steps of:
    loading a nanoparticle with said pharmacologically active substance by absorption, adsorption, or incorporation thereto;
    coating said loaded nanoparticle with a surfactant selected from a group consisting of polyoxyethylene 20 sorbitan monolaurate, polyoxyethylene 20 sorbitan monopalmitate, polyoxyethylene 20 sorbitan monostearate, polyoxyethylene 20 sorbitan monooleate, and mixtures thereof;
    administering said coated nanoparticle to said mammal in a manner which allows said drug to enter the bloodstream whereby said pharmacologically active substance reaches and crosses the blood-brain barrier; and
    allowing said pharmacologically active substance to achieve said pharmacological effect.

2. The method of claim 1 wherein said loading step comprises mixing said pharmacologically active substance and said nanoparticle in solution and allowing sufficient time for an amount of said pharmacologically active substance which provides the pharmacological activity of said active substance to be adsorbed by said nanoparticle.

3. The method of claim 1 wherein said loading step comprises incorporation of the pharmacologically active substance into the nanoparticles by manufacturing the nanoparticles in the presence of said pharmacologically active substance.

4. The method of claim 1 wherein said coating step comprises mixing said loaded nanoparticles with a solution of said surfactant in a solution and allowing sufficient time to allow said surfactant to coat said nanoparticle.

5. The method of claim 1 wherein said administration step comprises oral administration.

6. The method of claim 1 wherein said administration effect comprises intravenous administration.

7. The method of claim 1 wherein said nanoparticle comprises a synthetic polymeric particle from about 1 to 1000 nm in diameter.

8. The method of claim 7 wherein said synthetic polymeric nanoparticle are formed of a polymer selected from the group consisting of acrylates, methacrylates, methylmethacrylates, cyanoacrylates, acrylamides, polylactates, polyglycolates, polyanhydrates, polyorthoesters, gelatin, albumin, polystyrenes, polyvinyls, polyacroleines, polyglutaraldehydes, and copolymers, and mixtures thereof.

9. The method of claim 7 wherein said nanoparticles are formed by a method selected from the group consisting of emulsion polymerization, interfacial polymerization, solvent evaporation, and cross-linking of polymers in solution.

10. The method of claim 1 wherein said pharmacologically active substance comprises a substance which has central nervous system activity but cannot cross the blood-brain barrier without modification or without a carrier.

11. The method of claim 1 wherein said pharmacologically active substance comprises a drug.

12. The method of claim 1 wherein said pharmacologically active substance comprises a diagnostic agent.

13. The method of claim 12 wherein said diagnostic agent is useful in the diagnosis for nuclear medicine and radiation therapy.

* * * * *